United States Patent
Brown et al.

(10) Patent No.: US 9,289,203 B2
(45) Date of Patent: Mar. 22, 2016

(54) METHOD AND APPARATUS TO RELOAD SUTURE ANCHORS

(71) Applicant: Biomet Sports Medicine, LLC, Warsaw, IN (US)

(72) Inventors: Robin Brown, Warsaw, IN (US); Daniel B. Smith, Warsaw, IN (US); Nathan A. Winslow, Warsaw, IN (US); David A. Nolan, Jr., Fort Wayne, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 247 days.

(21) Appl. No.: 13/794,258

(22) Filed: Mar. 11, 2013

(65) Prior Publication Data

US 2014/0257314 A1     Sep. 11, 2014

(51) Int. Cl.
*A61B 17/17* (2006.01)
*A61B 17/04* (2006.01)

(52) U.S. Cl.
CPC ............. *A61B 17/0401* (2013.01); *A61B 17/17* (2013.01); *A61B 2017/0406* (2013.01); *A61B 2017/0409* (2013.01); *A61B 2017/0416* (2013.01)

(58) Field of Classification Search
CPC .... A61B 17/04; A61B 17/17; A61B 17/1796; A61B 17/0401
USPC ....................................................... 606/96–98
See application file for complete search history.

(56) References Cited

U.S. PATENT DOCUMENTS

| | | | |
|---|---|---|---|
| 5,207,692 A | 5/1993 | Kraus et al. | |
| 5,250,055 A * | 10/1993 | Moore et al. | 606/148 |
| 5,520,702 A | 5/1996 | Sauer et al. | |
| 5,733,293 A | 3/1998 | Scirica et al. | |
| 5,810,848 A | 9/1998 | Hayhurst | |
| 5,897,564 A | 4/1999 | Schulze et al. | |
| 6,013,083 A * | 1/2000 | Bennett | 606/104 |
| 6,425,900 B1 | 7/2002 | Knodel et al. | |
| 6,447,524 B1 | 9/2002 | Knodel et al. | |
| 6,572,626 B1 | 6/2003 | Knodel et al. | |
| 6,626,916 B1 | 9/2003 | Yeung et al. | |
| 6,773,438 B1 | 8/2004 | Knodel et al. | |
| 6,974,466 B2 | 12/2005 | Ahmed et al. | |

(Continued)

FOREIGN PATENT DOCUMENTS

| | | |
|---|---|---|
| EP | 0599772 A1 | 6/1994 |
| WO | WO-2013181373 A2 | 12/2013 |

OTHER PUBLICATIONS

Invitation to Pay Additional Fees and, where Applicable, Protest Fee mailed Sep. 12, 2013 for PCT/US2013/043333 claiming benefit of U.S. Appl. No. 13/485,304, filed May 31, 2012.

(Continued)

*Primary Examiner* — Christopher Beccia
(74) *Attorney, Agent, or Firm* — Schwegman Lundberg & Woessner, P.A.

(57) ABSTRACT

A drill guide assembly for drilling a bone hole and implanting a suture anchor in the bone hole. The assembly includes a drill guide and a suture anchor. The drill guide includes a sidewall extending between a proximal end and a distal end of the drill guide. The sidewall defines a center cannulation configured to receive a drill. The suture anchor retention portion of the drill guide is configured to support a suture anchor for coupling with an inserter device pushed through the drill guide to implant the suture anchor in the bone hole.

19 Claims, 8 Drawing Sheets

(56) References Cited

U.S. PATENT DOCUMENTS

| | | |
|---|---|---|
| 7,048,748 B1 | 5/2006 | Ustuner |
| 7,160,314 B2 | 1/2007 | Sgro et al. |
| 7,485,124 B2 | 2/2009 | Kuhns et al. |
| 7,645,286 B2 | 1/2010 | Catanese, III et al. |
| 7,749,250 B2 | 7/2010 | Stone et al. |
| 7,758,594 B2 | 7/2010 | Lamson et al. |
| 7,758,612 B2 | 7/2010 | Shipp |
| 7,896,891 B2 | 3/2011 | Catanese, III et al. |
| 7,905,893 B2 | 3/2011 | Kuhns et al. |
| 8,128,657 B2 | 3/2012 | Shiono et al. |
| 8,157,815 B2 | 4/2012 | Catanese, III et al. |
| 8,236,011 B2 | 8/2012 | Harris et al. |
| 8,267,963 B2 | 9/2012 | Williams |
| 8,398,657 B2 | 3/2013 | Sauer |
| 2005/0288711 A1 | 12/2005 | Fallin et al. |
| 2006/0282081 A1 | 12/2006 | Fanton et al. |
| 2007/0203508 A1 | 8/2007 | White et al. |
| 2007/0276365 A1 | 11/2007 | Song et al. |
| 2008/0243143 A1 | 10/2008 | Kuhns et al. |
| 2010/0312258 A1 | 12/2010 | Shipp |
| 2011/0071556 A1 | 3/2011 | Shipp |
| 2011/0270280 A1 | 11/2011 | Saliman |
| 2011/0306989 A1 | 12/2011 | Darois et al. |
| 2012/0290005 A1 | 11/2012 | Martin et al. |
| 2013/0023930 A1 | 1/2013 | Stone et al. |
| 2013/0325011 A1* | 12/2013 | Cleveland et al. .............. 606/80 |
| 2013/0325063 A1 | 12/2013 | Norton et al. |
| 2015/0005820 A1 | 1/2015 | Finley et al. |

OTHER PUBLICATIONS

"JuggerKnot™ Soft Anchor. Labral Repair," brochure. Biomet Sports Medicine (Apr. 2011) 12 sheets.

"JuggerKnot™ Soft Anchor. It's Small. It's strong. And it's all suture . . . " Ordering Information brochure. Biomet Sports Medicine (Jun. 2011) 2 sheets.

"JuggerKnot™ Soft Anchor Midfoot Repair," brochure. Biomet Sports Medicine (Jul. 2011) 12 sheets.

International Preliminary Report on Patentability and Written Opinion mailed Dec. 11, 2014 for PCT/US2013/043333 claiming benefit of U.S. Appl. No. 13/485,304, filed May 31, 2012.

International Search Report and Written Opinion mailed Jan. 14, 2014 for PCT/US2013/043333 claiming benefit of U.S. Appl. No. 13/485,304, filed May 31, 2012.

* cited by examiner

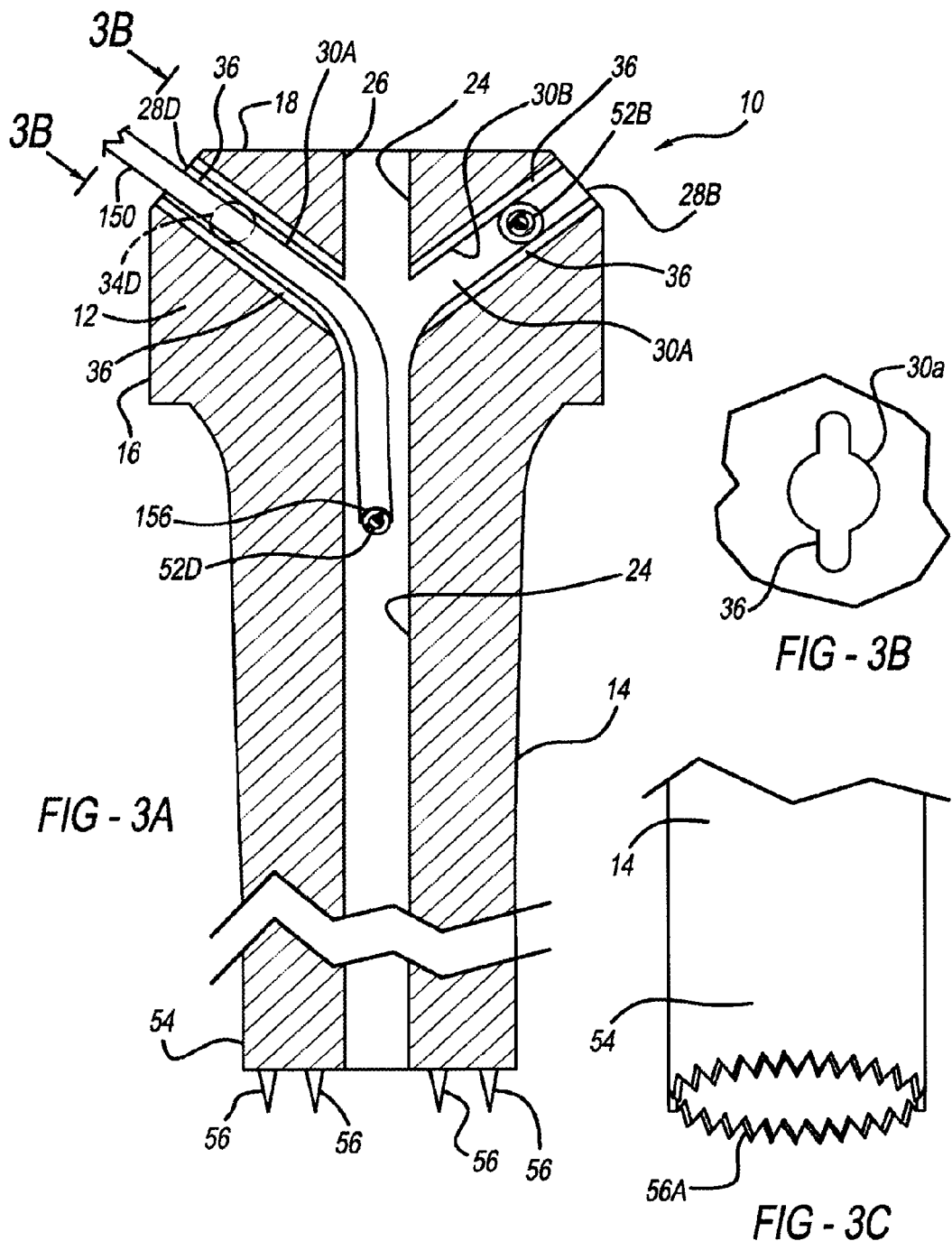

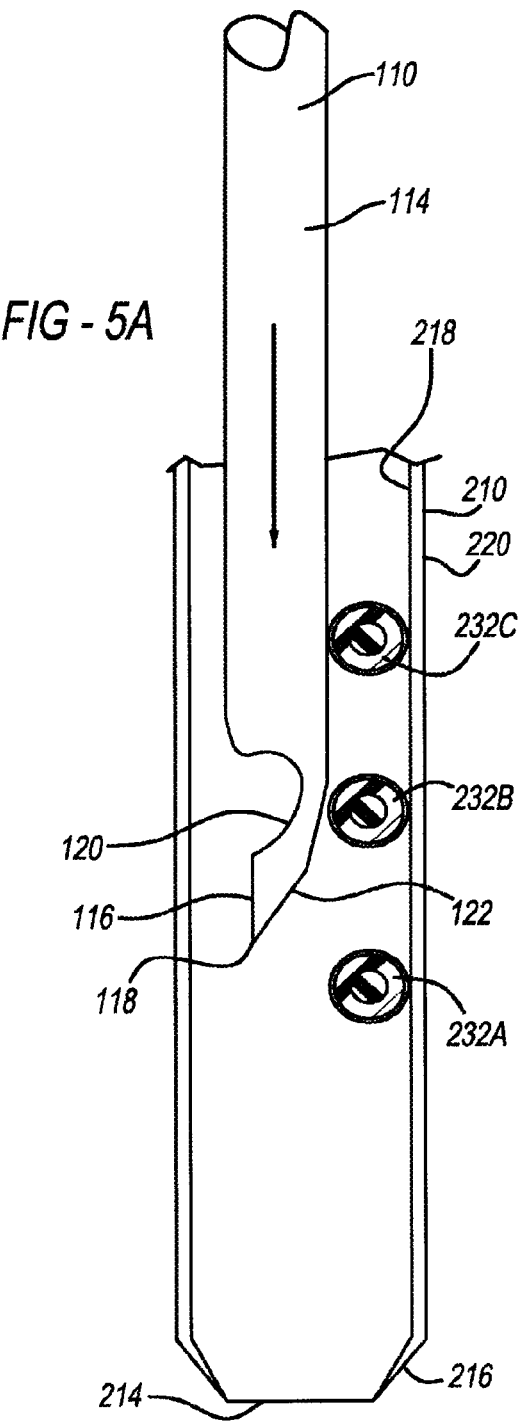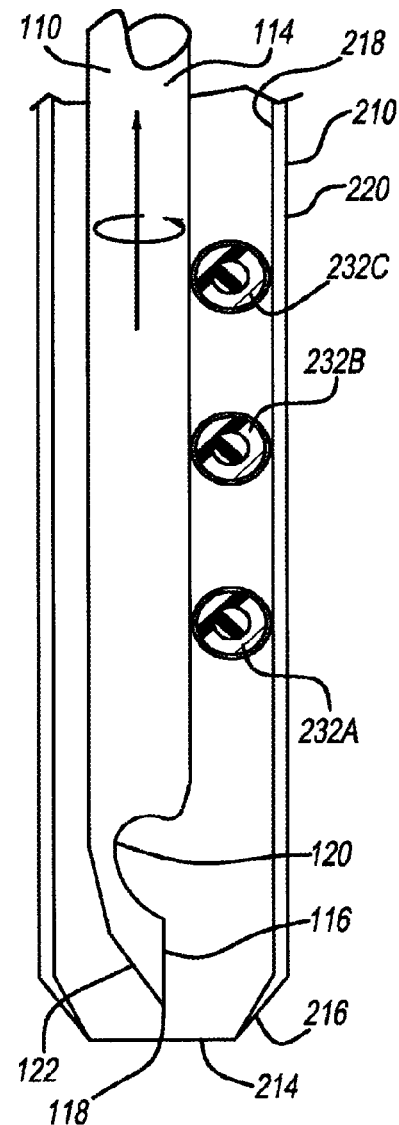

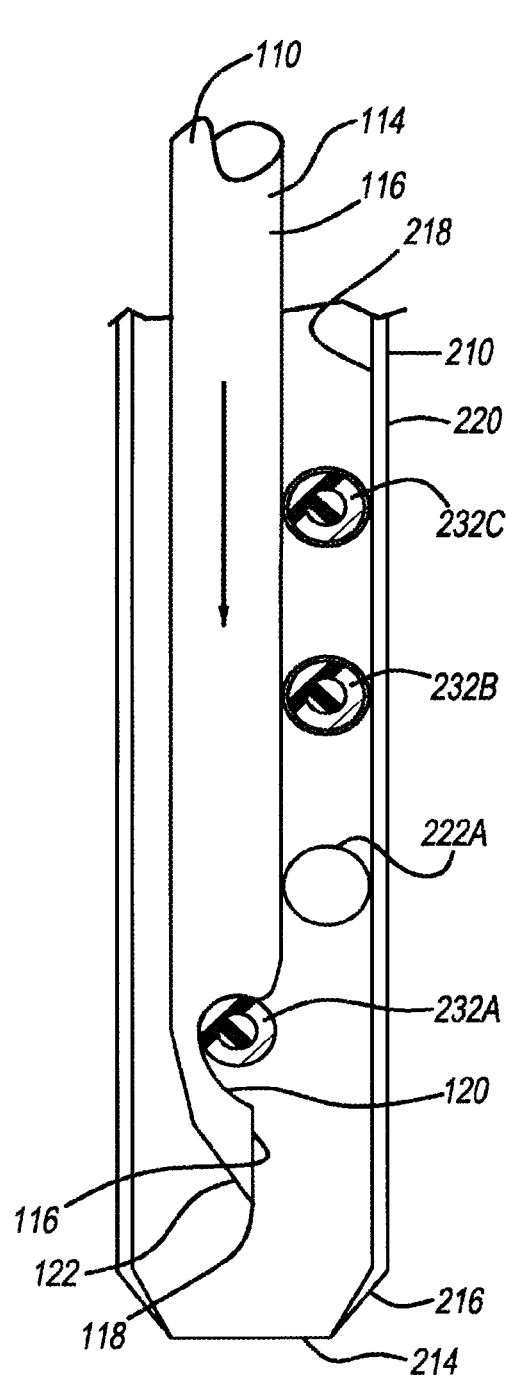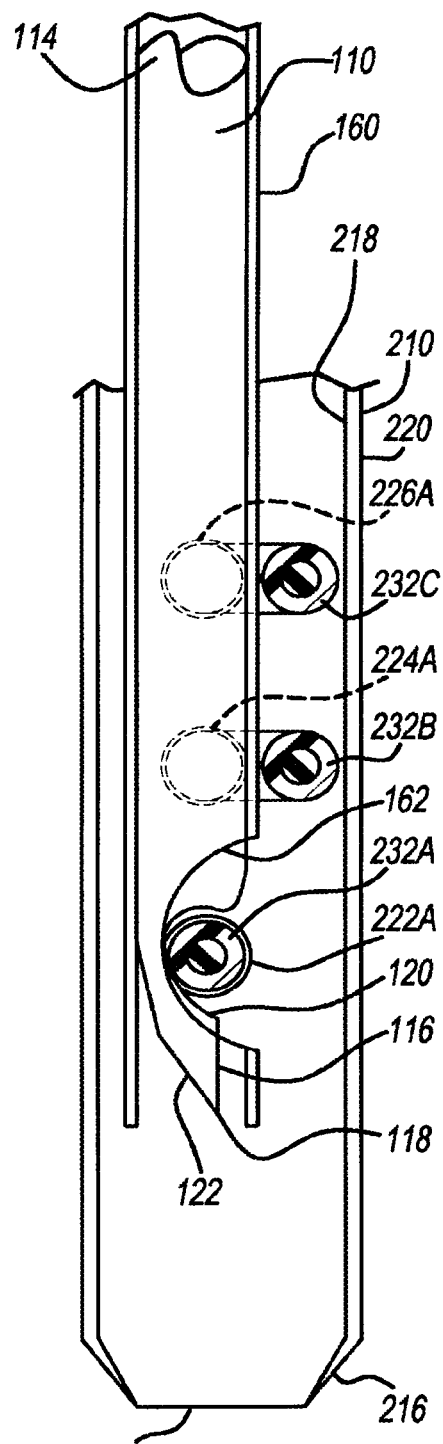

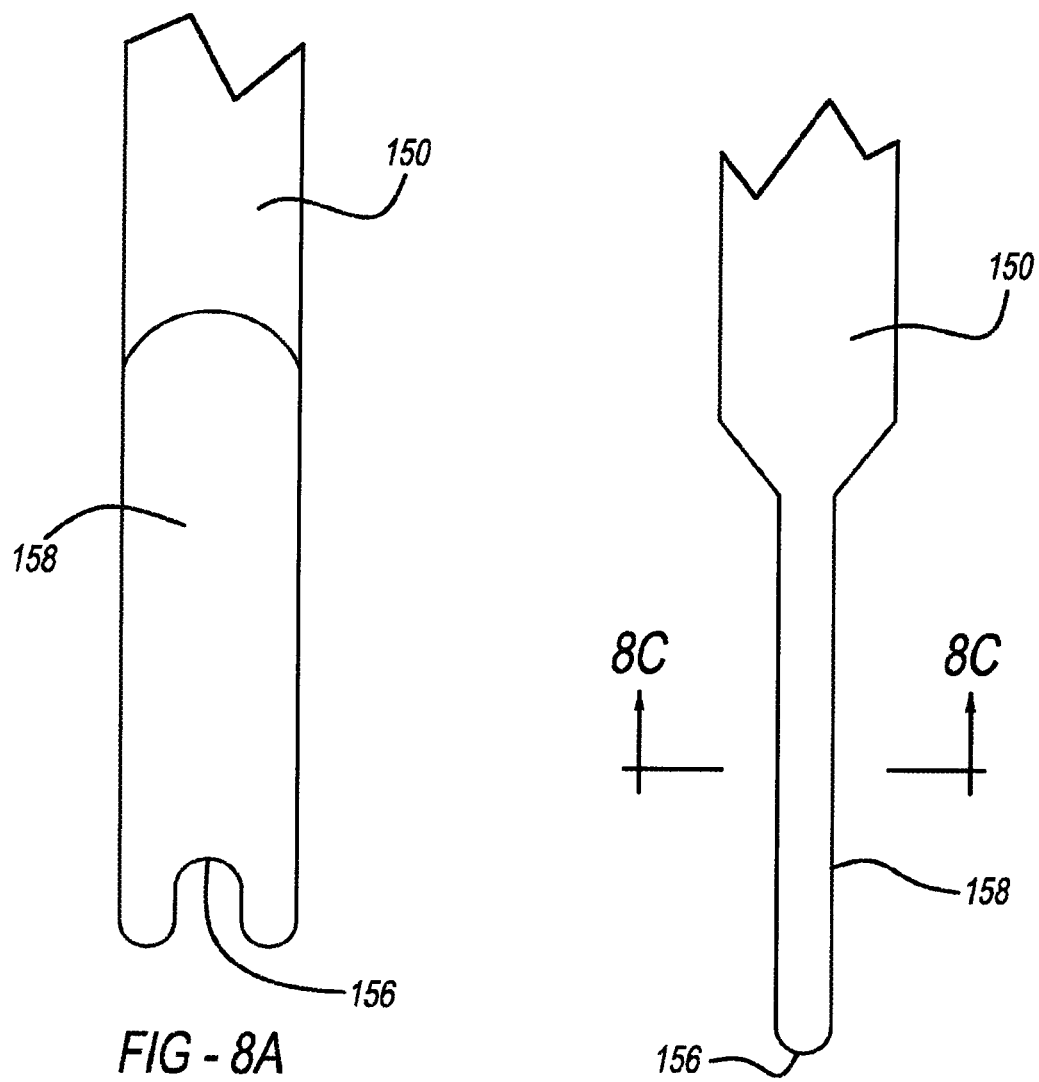
FIG - 8A
FIG - 8B
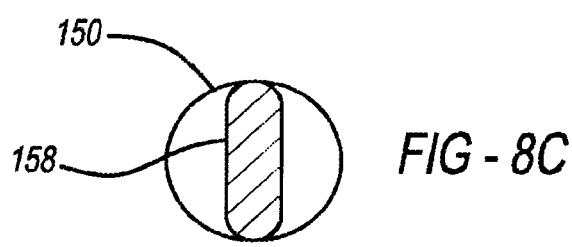
FIG - 8C

METHOD AND APPARATUS TO RELOAD SUTURE ANCHORS

FIELD

The present disclosure relates to a method and apparatus for reloading suture anchors.

BACKGROUND

This section provides background information related to the present disclosure, which is not necessarily prior art.

To implant a suture anchor at an implant site, an inserter is often used. Any suitable inserter can be used, such as the inserter offered by Biomet, Inc. for use with its JuggerKnot™ soft anchor. The suture anchor, such as the JuggerKnot™ anchor, is typically pre-loaded on the inserter because it may be inconvenient to load in the operating room. After the suture anchor is implanted, the inserter is typically disposed of. A different inserter is therefore used for each suture anchor, which can increase cost and waste. A device for quickly and easily reloading a suture anchor onto an inserter would make it possible to use a single inserter to implant multiple suture anchors.

SUMMARY

This section provides a general summary of the disclosure, and is not a comprehensive disclosure of its full scope or all of its features.

The present teachings provide for a drill guide assembly for drilling a bone hole and implanting a suture anchor in the bone hole. The assembly includes a drill guide and a suture anchor. The drill guide includes a sidewall extending between a proximal end and a distal end of the drill guide. The sidewall defines a center cannulation configured to receive a drill. The suture anchor retention portion of the drill guide is configured to support a suture anchor for coupling with an inserter device pushed through the drill guide to implant the suture anchor in the bone hole.

The present teachings also provide for a drill guide assembly for drilling a bone hole and implanting a suture anchor in the bone hole. The drill guide of the assembly includes a head and a shaft. The head defines a cannulation, an inserter passageway extending between an outer surface of the head and the cannulation, and a suture passageway that intersects the inserter passageway. The shaft extends from the head. The shaft further defines the cannulation. The cannulation is configured to guide a drill to the bone through the head and the shaft. The suture passageway is configured to support the suture anchor therein such that the suture anchor extends across the inserter passageway. The suture passageway is further configured to enable an inserter device to be pushed through the inserter passageway and couple to the suture anchor to push the suture anchor through the inserter passageway and through the cannulation to implant the anchor in a bone hole.

The present teachings further provide for a drill guide assembly for drilling a bone hole and implanting a suture anchor in the bone hole. The assembly includes a drill guide with a proximal end, a distal end, a sidewall, and a suture anchor retention portion. The sidewall extends between the proximal end and the distal end. The sidewall defines a cannulation that extends from the proximal end to the distal end. The suture anchor retention portion is defined by the sidewall proximate to the distal end. The suture anchor retention portion is configured to support the suture anchor within the cannulation. An inserter device includes a handle, a shaft extending from the handle, and a hook at a distal end of the handle configured to couple with the suture anchor. The cannulation is configured to guide a drill to the bone to drill the bone hole. The cannulation is configured to guide the inserter device through the cannulation to the bone hole. The hook of the inserter device couples with the suture anchor as the hook is moved past the suture anchor to the distal end of the drill guide.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3A is a cross-sectional view taken along line 3-3 of FIG. 2;

FIG. 3B is a cross-sectional view of an inserter passageway of the drill guide of FIG. 1;

FIG. 3C illustrates a modified end portion of the drill guide of FIG. 1;

FIG. 5A is a cross-sectional view of the drill guide of FIG. 4A;

FIG. 5B is similar to FIG. 5A, but with the inserter rotated 180 degrees after being moved such that a hook of the inserter is distal to a most distal suture anchor;

FIG. 5C illustrates the inserter at a distal position and coupled to the suture anchor for implantation in a bone hole;

FIG. 6 illustrates the inserter coupled with the most distal suture anchor of the drill guide, the inserter is seated within a sheath.

FIG. 8A illustrates a distal end of an inserter according to the present teachings;

FIG. 8B is a side view of the inserter of FIG. 8A; and

FIG. 8C is a cross-sectional view taken along line 8C-8C of FIG. 8B.

Corresponding reference numerals indicate corresponding parts throughout the several views of the drawings.

DETAILED DESCRIPTION

Example embodiments will now be described more fully with reference to the accompanying drawings.

Figure 1:
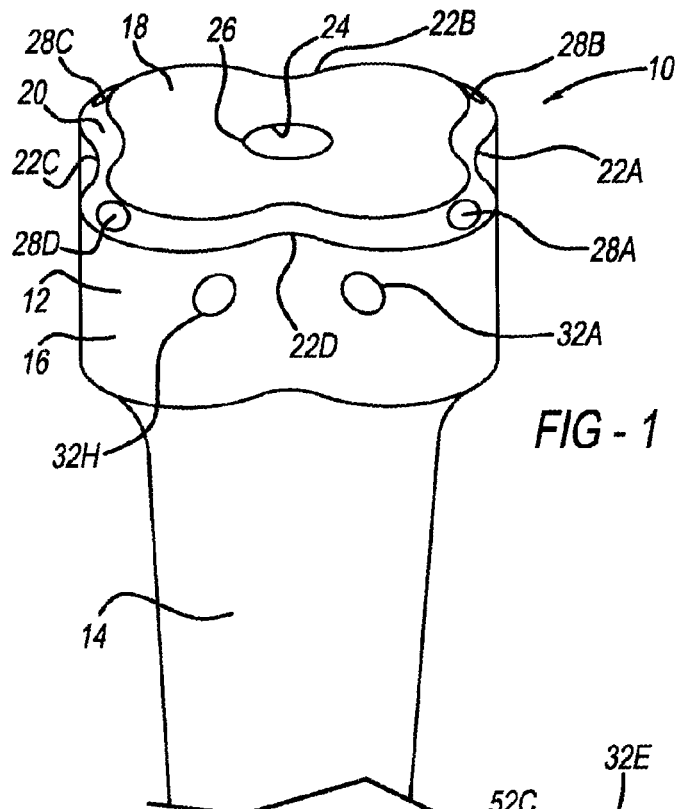
FIG. 1 is a perspective view of a drill guide according to the present teachings.
Figure 2:
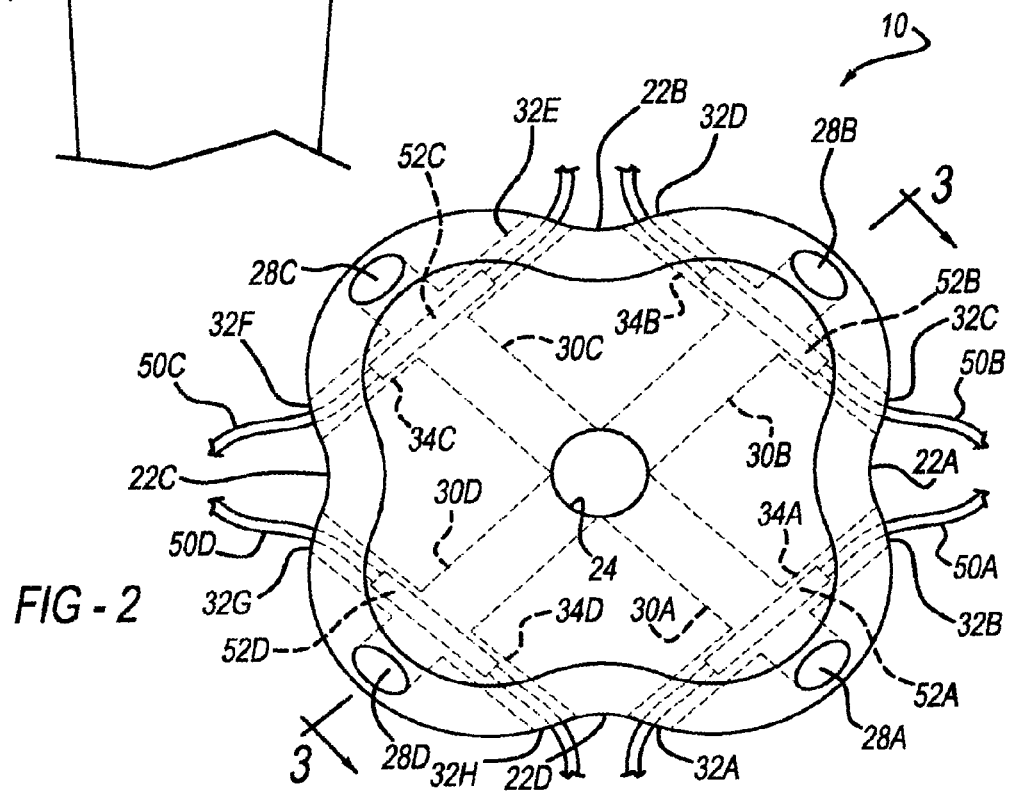
FIG. 2 is a top view of the drill guide of FIG. 1.

With initial reference to FIGS. 1-3, a drill guide according to the present teachings is illustrated at reference numeral 10. The drill guide 10 generally includes a head 12 and a shaft 14 extending therefrom. The head 12 generally includes a side surface 16, a proximal surface 18 and an angled surface 20, which generally combine to define an outer surface of the head 12. The side surface 16 extends in a plane generally perpendicular to a plane in which the proximal surface 18 extends. The angled surface 20 is between the side surface 16 and the proximal surface 18. The angled surface 20 extends from the side surface 16 to the proximal surface 18 and is angled with respect to each of the side surface 16 and the proximal surface 18. The angled surface 20 need not be planar, and thus can be rounded.

The side surface 16 is tapered inward at a first tapered portion 22A, a second tapered portion 22B, a third tapered portion 22C, and a fourth tapered portion 22D. Although the tapered portions 22A, 22B, 22C, and 22D are described as "tapered," they may also be scalloped-shaped. The first tapered portion 22A is generally opposite to the third tapered portion 22C, and the second tapered portion 22B is generally opposite to the fourth tapered portion 22D. The first tapered portion 22A is generally perpendicular to both the second tapered portion 22B and the fourth tapered portion 22D. The third tapered portion 22C is also generally perpendicular to both the second tapered portion 22B and the fourth tapered portion 22D. The first, second, third, and fourth tapered portions 22A-22D may make the head 12 more ergonomic and easier for the surgeon to hold and/or manipulate. The head 12 can have any suitable shape to make it more ergonomic, such as a circular shape, a square shape, etc.

Both the head 12 and the shaft 14 define a center cannulation 24, which extends through each of the head 12 and the shaft 14 to provide a guide for a drill suitable to drill a hole in bone. At the proximal surface 18, the center cannulation 24 is defined by a center aperture 26. The center cannulation 24 extends from the center aperture 26 to a distal end (not shown) of the drill guide, such that the center cannulation 24 extends entirely through the head 12 and the shaft 14.

The head 12 further defines a plurality of inserter apertures 28A-28D at the angled surface 20. As illustrated in FIG. 2, for example, extending from the first inserter aperture 28A is a first inserter passageway 30A defined by the head 12. Extending from the second inserter aperture 28B is a second inserter passageway 30B. Extending from the third inserter aperture 28C is a third inserter passageway 30C. Extending from the fourth inserter aperture 28D is a fourth inserter passageway 30D. Each of the inserter passageways 30A-30D extend at an angle from their respective inserter apertures 28A-28D to the center cannulation 24 at a point in the head 12, as illustrated in FIG. 3A.

The inserter apertures 28A-28D and corresponding inserter passageways 30A-30D are evenly spaced apart around the head 12. For example and as illustrated in FIG. 2, adjacent inserter passageways 30A-30D are arranged at about a 90 degree angle relative to one another, and generally at corners of the head 12 such that passageway 30A is between the first and fourth tapered portions 22A/22D, passageway 30B is between the first and the second tapered portions 22A/22B, passageway 30C is between the second and the third tapered portions 22B/22C, and passageway 30D is between the third and the fourth tapered portions 22C and 22D. For example, first inserter passageway 30A is spaced apart about 90 degrees relative to the second inserter passageway 30B. The inserter passageways 30A-30D extend from the surface 20 toward the shaft 14, and thus generally extend downward from the surface 20 and away from the proximal surface 18. The inserter apertures 28A-28D need not be at the same level, height, or distance from the proximal surface 18, but can be staggered, such that one or more of the inserter apertures 28A-28D are closer or further from the proximal surface 18 than the others.

Figure 4A:
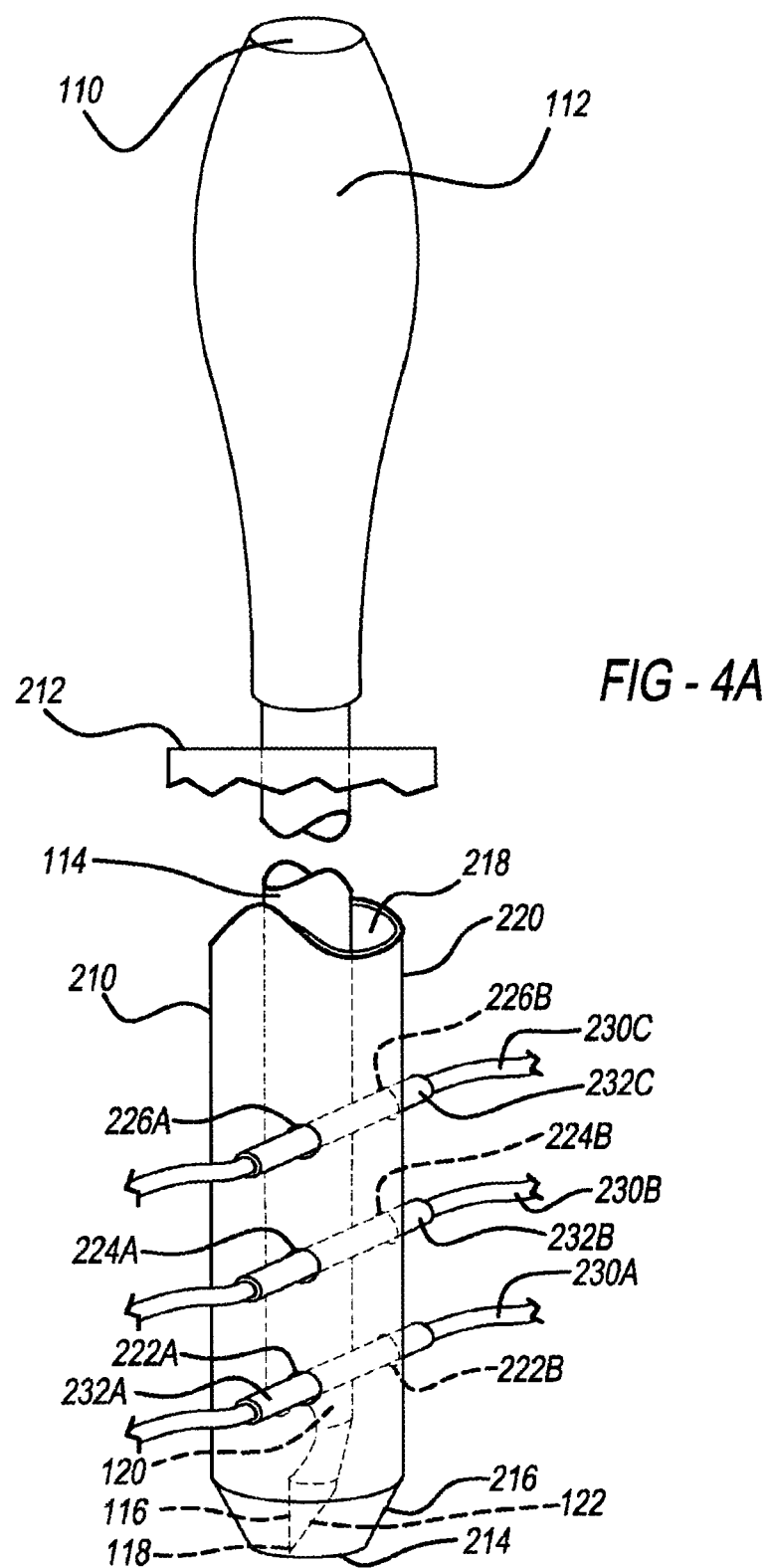
FIG. 4A is a perspective view of another drill guide according to the present teachings and a suture anchor inserter.

The inserter apertures 28A-28D and the inserter passageways 30A-30D are generally sized and shaped to receive a shaft of a suture anchor inserter, such as shaft 114 of inserter 110, or planar portion 158 of inserter 150. The inserter 110 is illustrated in FIG. 4A and the inserter 150 is illustrated in FIGS. 8A-8C. The inserter passageways 30A-30D can have a circular cross-section or a cross-section keyed to receive the inserter 150 at a particular orientation that will guide the inserter 150 into contact with suture anchors 52A-52D at a desired orientation to ensure cooperation therebetween. For example, one or more of the inserter passageways 30A-30D can be keyed as illustrated in FIG. 3B to define a slot 36 sized and shaped to receive a planar portion 158 of the inserter 150 (see FIGS. 8A, 8B, and 8C) proximate to the hook 156 of the inserter 150.

The head 12 further defines a plurality of suture apertures 32A-32H and a plurality of suture passageways 34A-34D. The suture apertures 32A-32H are defined by the side surface 16 of the head 12 and are generally positioned such that one of the inserter apertures 28A-28D is between a pair of the suture apertures 32A-32H. For example, the first inserter aperture 28A is between suture aperture 32A and suture aperture 32B. Second inserter aperture 28B is between suture aperture 32C and suture aperture 32D. Third inserter aperture 28C is between suture aperture 32E and suture aperture 32F. Fourth inserter aperture 28D is between suture apertures 32G and 32H.

Each suture passageway 34A-34D extends between a pair of the suture apertures 32A-32H, and intersects one of the inserter passageways 30A-30D. Specifically, suture passageway 34A extends between suture apertures 32A and 32B and intersects inserter passageway 30A. Suture passageway 34B extends between suture apertures 32C and 32D and intersects inserter passageway 30B. Suture passageway 34C extends between suture apertures 32E and 32F and intersects inserter passageway 30C. Suture passageway 34D extends between suture apertures 32G and 32H and intersects inserter passageway 30D. Each of the suture passageways 34A-34D are suture anchor retention portions.

Each of the suture passageways 34A-34D are sized and shaped to receive and retain one of sutures 50A-50D therein. Each of the sutures 50A-50D include a suture anchor 52A-52D respectively. Any suitable type of suture can be used, such as a suture with a soft anchor capable of passing through the inserter passageways 30A-30D and the center cannulation 24. While the examples described herein include a soft anchor, a hard anchor may be used as well. The anchors 52A-52D are arranged such that they extend across the inserter passageway 30A-30D associated therewith. Each of the suture passageways 34A-34D generally intersect the inserter passageway 30A-30D associated therewith at a right angle, and thus a longitudinal axis of each of the anchors 52A-52D intersects and is generally perpendicular to the longitudinal axis of the associated inserter passageway 30A-30D. Each of the suture passageways 34A-34D extend parallel to proximal surface 18 and perpendicular to the center aperture 26.

An exemplary method of using the drill guide 10 will now be described. The drill guide 10 is positioned proximate to a bone surface where a bone hole is to be drilled. A distal end 54 of the drill guide 10 can engage the bone surface and can include any suitable feature to facilitate engagement with the bone surface. For example, the distal end 54 can include suitable teeth 56, serrations 56A (FIG. 3C), or a roughened surface. The distal end 54 can also be flat. A suitable bone drill is then inserted through center aperture 26 into the center cannulation 24. The drill is moved through the center cannulation 24 to the bone, and the bone hole is then drilled therein. Once the drill is removed from within the center cannulation 24, one of the anchors 52A-52D of the sutures 50A-50D can be implanted in the bone hole.

The sutures 50A-50D can be provided preloaded in the drill guide 10 by the manufacturer, or can be re-loaded into the suture passageways 34A-34D subsequent to implantation into the bone. Furthermore, after the sutures 50A-50D are implanted as described herein, additional sutures 50A-50D may be loaded into the suture passageways 34A-34D, thus allowing the drill guide 10 to be reused. Although four suture passageways 34A-34D are illustrated, any suitable number of suture passageways can be provided, such as more or less than four. Additional suture passageways 34A-34D can be included with the device 10 in any suitable manner, such as distally below the suture passageways 34A-34D and vertically aligned therewith.

The suture anchors 52A-52D can be implanted in the bone hole using any suitable inserter device, such as the inserter 110 of FIG. 4A or the inserter 150 described in U.S. patent application Ser. No. 13/485,304 ("'304 Application") titled "Suture Anchor Reload," filed on May 31, 2012 and assigned to Biomet of Warsaw, Ind. The '304 Application is incorporated herein by reference. The inserter 110 or 150 ("'304 Application") is passed through, for example, the first inserter aperture 28A such that a coupling portion or device at the distal end of the inserter 110/150, such as hook 120 of the inserter 110 or the hook 156 of the inserter 150 ("'304 Application") couples with the anchor 52A. The inserter 110 or 150 is then pushed through the inserter passageway 30A and into the center cannulation 24, thereby pushing the anchor into the center cannulation 24 as well. Because the inserter passageway 30A is angled with respect to the center cannulation 24, the shaft 114 of the inserter 110 or the shaft 152 of the inserter 150 ("'304 Application") is flexible. The anchor 52A is pushed through the center cannulation 24 into the bone hole to implant the anchor 52A. The drill guide 10 can then be moved to another location on the bone to drill another bone hole and implant another one of the anchors 52B-D in a similar manner.

With reference to FIG. 4A, additional details of the inserter 110 will now be described. The inserter 110 generally includes a handle 112 and a shaft 114 extending therefrom. The tip 116 is at a distal end of the shaft 114. The tip 116 includes a pointed end 118, sufficient to allow the inserter 110 to be impacted into the bone without pre-drilling the bone hole to secure the anchors 52A-52D within the bone hole. The pointed end 118 also facilitates movement of the shaft 114 past the anchors 52A-52D because the narrow, pointed end 118 is oriented away from suture anchors 232A-232C during insertion of the shaft 114 through the drill guide 210. Hook 120 is proximate to the pointed end 118. The hook 120 is configured to couple with any of the anchors 52A-52D to direct the anchors 52A-52D into the bone hole. The tip 116 includes a slanted surface 122 on a side of the tip opposite to the hook 120. As described herein, the slanted surface 122 clears the anchors 52D out of the way of the inserter 110 as the inserter is initially inserted within the drill guide 210 or 310, for example.

Figure 4B:
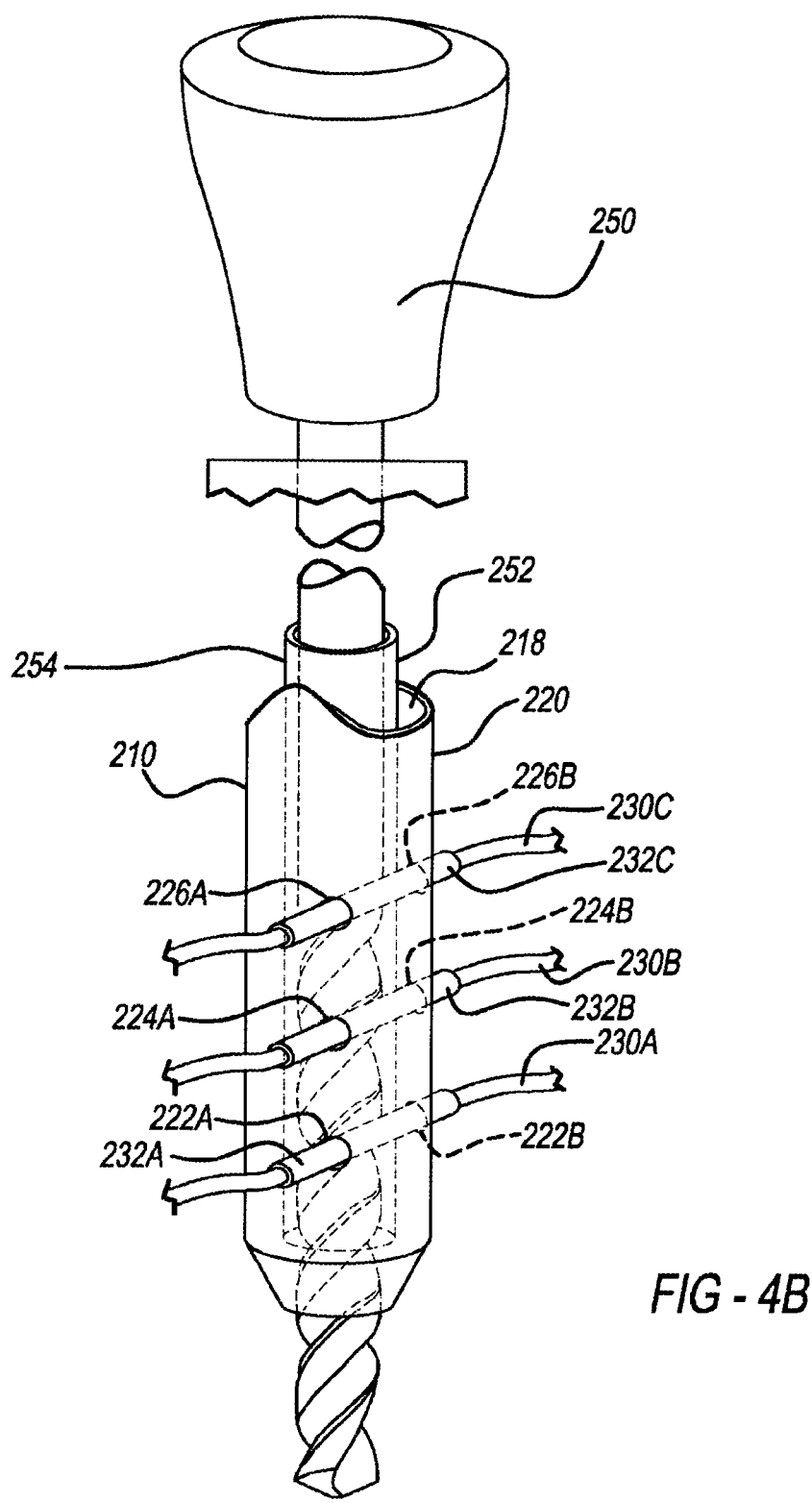
FIG. 4B is a perspective view of the drill guide of FIG. 4A including a drill and a protective sleeve therein.

With continued reference to FIG. 4A, an additional drill guide according to the present teachings is illustrated at reference numeral 210. The drill guide 210 generally includes a head 212 at a proximal end of the drill guide 210 and a tip 214 at a distal end of the drill guide 210. Proximate to the tip 214 is a tapered portion 216 of the drill guide 210. The drill guide 210 includes a center cannulation 218 defined by sidewall 220, which extends from the head 212 to the tip 214. The center cannulation 218 is configured to accommodate and guide a suitable drill, as well as the shaft 114 of the inserter 110, or any other suitable inserter including the inserter 150 of the '304 application. To protect the sutures 230A, 230B, and 230C from a drill 250, a protective sheath 252 can be included, as illustrated in FIG. 4B. The protective sheath 252 can include a tubular portion 254 with an outer diameter smaller than an inner diameter of the drill guide 210. A clearance for the sutures 230A, 230B, and 230C is defined between the sheath 252 and the sidewall 220 of the drill guide 210. The drill guide 210 can be a punch guide for applications where the sutures 230A, 230B, and 230C are impacted into bone using the inserter 110 without predrilling.

A first pair of apertures 222A and 222B are defined by the drill guide 210 proximate to the tip 214. The apertures 222A and 222B are aligned with one another and formed on opposite sides of the center cannulation 218 in order to suspend suture 230A and associated suture anchor 232A within and across the center cannulation 218. The apertures 222A and 222B can be arranged 180 degrees relative to each other, or less, so that the suture anchor 232A extends through a longitudinal axis of the center cannulation 218 or proximate to the longitudinal axis. Alternatively, the apertures 222A and 222B can be positioned such that the suture anchor 232A does not extend directly through the longitudinal axis of the center cannulation 218, but is offset therefrom in order to accommodate the shaft 114 of the inserter 110 within the center cannulation 218.

The drill guide 210 can further include a second pair of apertures 224A and 224B, as well as a third pair of apertures 226A and 226B. The second pair of apertures 224A/224B and the third pair of apertures 226A/226B are similar to the first pair of apertures 224A/224B. The second pair of apertures 224A and 224B are arranged proximal to the first pair of apertures 222A and 222B. The third pair of apertures 226A and 226B are arranged proximal to the first pair of apertures 222A and 222B, as well as the second pair of apertures 224A and 224B. Therefore, the second pair of apertures 224A and 224B are arranged between the first pair of apertures 222A and 222B and the third pair of apertures 226A and 226B. The second pair of apertures 224A/224B and the third pair of apertures 226A/226B are similar to the first pair of apertures 222A/222B. Each of the pairs of apertures 222A/222B, 224A/224B, and 226A/226B are thus suture anchor retention portions. While the drill guide 210 is illustrated as including three pairs of apertures 222A/222B, 224A/224B and 226A/226B, any suitable number of aperture pairs can be included. Each of the pairs of apertures 222A/222B, 224A/224B, and 226A/226B are radially aligned about the sidewall 220 and arranged parallel to one another.

Use of the drill guide 210 to implant the first suture anchor 232A, the second suture anchor 232B, and the third suture anchor 232C will now be described. The drill guide 210 is positioned at a portion of a bone where a bone hole is to be formed. A suitable drill bit of a drill is inserted through the center cannulation 218, within the protective sheath 252 to drill a bone hole. The drill bit can be encased within a sheath to guard against damage of the suture anchors 232A-232C. A distal end of the sheath can include an angled tip to move the suture anchors 232A-232C to the side when the drill bit is inserted.

After the bone hole has been formed, the drill is removed and the inserter 110, or any other suitable inserter such as the inserter 150 of the '304 application, is inserted into the center cannulation 218. As illustrated in FIG. 5A, the inserter 110 is initially inserted such that the hook 120 faces away from the suture anchors 232A-232C, and so that the slanted surface 122 contacts the suture anchors 232A-232C to move them to the side of the inserter 110. After the hook 120 has passed the distal-most suture anchor 232A, the inserter 110 is rotated 180 degrees such that the hook 120 faces the direction of the distal-most suture anchor 232A, as illustrated in FIG. 5B. To implant the first suture anchor 232A for example, the inserter 110 is moved upward in the proximal direction such that the hook 120 moves to and couples with the suture anchor 232A, as illustrated in FIG. 5C. To implant the suture anchor, the inserter 110 is then moved in the opposite direction towards the tip 214 with the suture anchor 232A coupled thereto. The inserter 110 is further pushed through the drill guide 210 to move the suture anchor 232A through the tip 214 and into the bone hole where the suture anchor 232A is impacted into the bone hole with the inserter 110. The second suture anchor 232B and the third suture anchor 232C can be implanted into other bone holes in a similar manner.

With reference to FIG. 6, a sheath 160 can be provided to house the shaft 114 of the inserter 110 within the drill guide 210. The sheath 160 prevents the hook 120 from contacting the suture anchors 232A-232C as the shaft 114 is initially inserted within the drill guide 210. The sheath 160 can be coupled to the inserter 110 in any suitable manner, such as to the handle 112 or a proximal end of the shaft 114. The sheath 160 defines a window 162 at a distal end thereof. The window 162 allows the hook 120 to couple with the suture anchors 232A-232C. For example, when the sheath 160 is moved to the distal suture anchor 232A, the suture anchor 232A will be biased to move within the window 162, particularly when the apertures 222A and 222B are arranged 180 degrees from one another such that the suture anchor 232A passes through the longitudinal axis of the drill guide 210. With the suture anchor 232A seated within the window 162, the shaft 114 is moved, typically proximally, so that the hook 120 couples with the suture anchor 232A. The suture anchor 232A is then implanted as described above.

Figure 7:
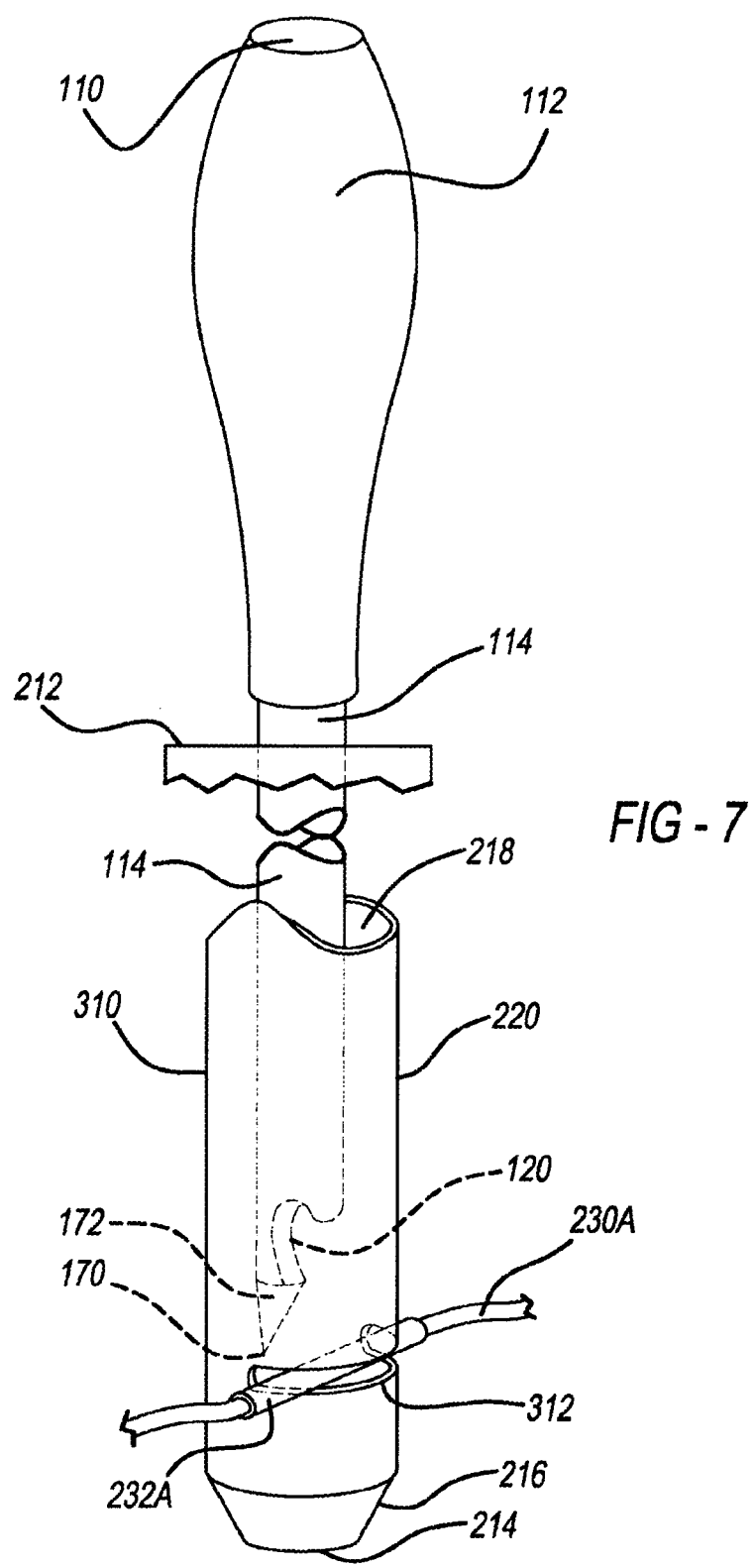
FIG. 7 illustrates an additional drill guide according to the present teachings and the inserter.

An additional drill guide according to the present teachings is illustrated in FIG. 7 at reference numeral 310. The drill guide 310 is similar to the drill guide 210, and thus features in common between the drill guide 210 and the drill guide 310 are illustrated with common reference numerals. The description of the like features set forth above with respect to the drill guide 210 also applies to the similar features of the drill guide 310. Unlike the drill guide 210, the drill guide 310 includes a slot 312, which is defined by the sidewall 220. The slot 312 serves as a suture retention portion for one of the sutures 230A-230C. The inserter 110 can be used to implant the suture 230A mounted to the drill guide 310 in the same manner described above with respect to the drill guide 210. When there is only one suture anchor 232A to couple with as illustrated, the shaft 114 can be inserted with the hook 120 facing the suture anchor 232A because there is no other suture anchor to avoid. Furthermore, the shaft 114 can have a modified tip 172 in which the slanted surface 122 is not included and pointed end 170 is opposite to the hook 120, thereby facilitating cooperation between the suture anchor 232A and the hook 120.

Any suitable number of slots 312, such as a plurality of vertically arranged slots 312, can be provided. After the suture 230A mounted to the drill guide 310 has been implanted, additional sutures 230 can be easily seated within the slot 312 for implantation thereof using the inserter 110. The sutures 230 can be manually placed into the slot 312 to facilitate coupling with the hook 120.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A drill guide assembly for drilling a bone hole and implanting a suture anchor in the bone hole comprising:
    a drill guide, including:
        a sidewall extending between a proximal end and a distal end of the drill guide, the sidewall defining a cannulation configured to receive a drill;
        an inserter passageway extending between an outer surface of the drill guide and the cannulation; and
        a suture anchor retention portion including a suture passageway that extends between a pair of opposing suture apertures defined by the sidewall and intersects the inserter passageway, the suture anchor retention portion configured to support a suture anchor for coupling with an inserter device pushed through the inserter passageway to implant the suture anchor in the bone hole.

2. The drill guide assembly of claim 1, wherein the inserter device includes a flexible shaft and a suture coupling portion at a distal end of the flexible shaft.

3. The drill guide assembly of claim 1, wherein the pair of opposing apertures are configured to support the suture anchor at the sidewall.

4. The drill guide assembly of claim 1, wherein the suture anchor retention portion includes a slot defined by the sidewall configured to support the suture anchor at the sidewall.

5. The drill guide assembly of claim 1, wherein the suture passageway is generally perpendicular to the inserter passageway at about a right angle.

6. A drill guide assembly for drilling a bone hole and implanting a suture anchor in the bone hole, a drill guide of the assembly comprising:
    a head defining a cannulation, an inserter passageway extending between an outer surface of the head and the cannulation, and a suture passageway that intersects the inserter passageway; and
    a shaft extending from the head, the shaft further defines the cannulation, the cannulation configured to guide a drill to the bone through the head and the shaft;
    wherein the suture passageway is configured to support the suture anchor therein such that the suture anchor extends across the inserter passageway, the suture passageway further configured to enable an inserter device to be pushed through the inserter passageway and couple to the suture anchor to push the suture anchor through the inserter passageway and through the cannulation to implant the anchor in a bone hole.

7. The drill guide assembly of claim 6, wherein the inserter passageway is a first inserter passageway, the head further defining:
    a second inserter passageway;
    a third inserter passageway; and
    a fourth inserter passageway;
    wherein each of the second, third, and fourth inserter passageways extend from the outer surface to the cannulation.

8. The drill guide assembly of claim 7, wherein neighboring ones of the first, second, third, and fourth inserter passageways are spaced apart at about 90° degrees.

9. The drill guide assembly of claim 7, wherein the outer surface of the head includes a side surface, a proximal surface, and an angled surface between the side surface and the proximal surface, the side surface extends in a first plane and the proximal surface extends in a second plane that is perpendicular to the first plane.

10. The drill guide assembly of claim 9, wherein each of the first, second, third, and fourth inserter passageways extend from the angled surface to the cannulation.

11. The drill guide assembly of claim 7, wherein the suture passageway is a first suture passageway, the head further defining:
   a second suture passageway intersecting the second inserter passageway;
   a third suture passageway intersecting the third inserter passageway; and
   a fourth suture passageway intersecting the fourth inserter passageway.

12. The drill guide assembly of claim 7, wherein the outer surface includes a first tapered portion between the first inserter passageway and the second inserter passageway, a second tapered portion between the second inserter passageway and the third inserter passageway, a third tapered portion between the third inserter passageway and the fourth inserter passageway, and a fourth tapered portion between the fourth inserter passageway and the first inserter passageway.

13. The drill guide assembly of claim 6, wherein the inserter device includes a flexible shaft, and a hook at a distal end of the flexible shaft, the hook configured to couple with the suture anchor.

14. A drill guide assembly for drilling a bone hole and implanting a suture anchor in the bone hole comprising:
   a drill guide including:
      a proximal end;
      a distal end;
      a sidewall extending between the proximal end and the distal end, the sidewall defining a cannulation that extends from the proximal end to the distal end; and
      a suture anchor retention portion defined by the sidewall proximate to the distal end, the suture anchor retention portion configured to support the suture anchor;
   an inserter device including a handle, a shaft extending from the handle, and a hook at a distal end of the handle configured to couple with the suture anchor;
   wherein the cannulation is configured to guide a drill to the bone to drill the bone hole; and
   wherein the cannulation is configured to guide the inserter device through the cannulation to the bone hole, the hook of the inserter device couples with the suture anchor as the hook is moved past the suture anchor to the distal end of the drill guide.

15. The drill guide assembly of claim 14, wherein the suture anchor retention portion is a first suture anchor retention portion proximate to the distal end, the drill guide assembly further comprising a second suture anchor retention portion, and a third suture anchor retention portion, the second suture anchor retention portion is between the first and the third suture anchor retention portions.

16. The drill guide assembly of claim 14, wherein the suture anchor retention portion includes a first aperture defined by the sidewall and a second aperture defined by the sidewall, the first aperture is aligned with the second aperture to retain the suture anchor extending therebetween.

17. The drill guide assembly of claim 15, wherein each of the first, second, and third suture anchor retention portions include a pair of opposing apertures.

18. The drill guide assembly of claim 16, wherein the suture anchor retention portion includes a slot defined by the sidewall.

19. The drill guide assembly of claim 18, wherein the slot is semicircular and extends through the sidewall to the cannulation to suspend the suture anchor across a portion of the cannulation.

\* \* \* \* \*